(12) United States Patent
Dillon et al.

(10) Patent No.: US 10,123,951 B2
(45) Date of Patent: Nov. 13, 2018

(54) DUAL PHASE MOUTHWASH COMPOSITIONS

(71) Applicant: Colgate-Palmolive Company, New York, NY (US)

(72) Inventors: Rensl Dillon, Ewing, NJ (US); Hameda Ahmed, South Plainfield, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/329,123

(22) PCT Filed: Jul. 25, 2014

(86) PCT No.: PCT/US2014/048315
§ 371 (c)(1),
(2) Date: Jan. 25, 2017

(87) PCT Pub. No.: WO2016/014090
PCT Pub. Date: Jan. 28, 2016

(65) Prior Publication Data
US 2017/0216157 A1 Aug. 3, 2017

(51) Int. Cl.
| | | |
|---|---|---|
| *A61K 8/03* | (2006.01) | |
| *A61K 8/86* | (2006.01) | |
| *A61K 8/891* | (2006.01) | |
| *A61K 8/60* | (2006.01) | |
| *A61K 8/06* | (2006.01) | |
| *A61Q 11/00* | (2006.01) | |

(52) U.S. Cl.
CPC .................. *A61K 8/03* (2013.01); *A61K 8/06* (2013.01); *A61K 8/60* (2013.01); *A61K 8/86* (2013.01); *A61K 8/891* (2013.01); *A61Q 11/00* (2013.01); *A61K 2800/87* (2013.01); *A61K 2800/882* (2013.01)

(58) Field of Classification Search
None
See application file for complete search history.

(56) References Cited

U.S. PATENT DOCUMENTS

| 5,130,124 A | 7/1992 | Merianos et al. |
|---|---|---|
| 6,465,521 B1 | 10/2002 | Rosenberg |
| 9,724,278 B2 | 8/2017 | Lambert et al. |

FOREIGN PATENT DOCUMENTS

| DE | 4215502 | | 11/1993 |
|---|---|---|---|
| DE | 1020060412291 A1 | * | 3/2006 |
| DE | 102006041291 | | 3/2008 |
| GB | 2355658 | | 5/2001 |
| JP | H08-325126 A | | 12/1996 |
| JP | H10-167943 A | | 6/1998 |
| JP | 10324619 A | * | 12/1998 |
| WO | WO 1997017939 | | 5/1997 |

OTHER PUBLICATIONS

Machine translation of DE1020060412291A1.*
Machine translation of JP 1032619 A.*
International Search Report and Written Opinion in International Application No. PCT/US2014/048315, dated Oct. 13, 2014.

* cited by examiner

*Primary Examiner* — Michael P Cohen

(57) ABSTRACT

The present invention provides a packaged mouthwash composition, the mouthwash composition comprising an aqueous phase and an oil phase; wherein the mouthwash composition is contained within a container, the aqueous phase being present as a first bulk layer and the oil phase being present as a second bulk layer, the first and second bulk layers being in contact with one another at an interface, with one of said layers being disposed on top of the other of said layers in the container; and wherein the mouthwash composition comprises a silicone oil.

27 Claims, No Drawings

DUAL PHASE MOUTHWASH COMPOSITIONS

BACKGROUND

Packaged dual phase mouthwash compositions having two visibly distinct layers, one on top of the other, are prone to suffering from problems with their cosmetic stability. In particular, such compositions have a tendency to develop a cloudy appearance over time, once the consumer has commenced use of a particular container of the mouthwash. Also, upon manufacture, the high-speed filling of the two layers into the mouthwash container tends to cause problems of increased opacity in the mouthwash composition. These problems of increased opacity can also arise during shipping of the product to retail outlets.

It would be desirable to provide mouthwash compositions having at least two layers disposed one on top of the other, in which the cosmetic acceptability of the composition is maintained over time, even once the consumer has started to use the particular container of mouthwash.

BRIEF SUMMARY

The present invention provides a packaged mouthwash composition, the mouthwash composition comprising an aqueous phase and an oil phase;

wherein the mouthwash composition is contained within a container, the aqueous phase being present as a first bulk layer and the oil phase being present as a second bulk layer, the first and second bulk layers being in contact with one another at an interface, with one of said layers being disposed on top of the other of said layers in the container;

and wherein the mouthwash composition comprises a silicone oil.

Optionally, the second bulk layer is disposed on top of the first bulk layer in the container.

Optionally, the silicone oil is in the aqueous phase.

Optionally, the composition comprises more than one silicone oil.

Optionally, the silicone oil is in the oil phase.

Optionally, the silicone oil is present in an amount of from 0.00005 to 0.1 weight %, based on the total weight of the mouthwash composition. Further optionally, the silicone oil is present in an amount of from 0.00005 to 0.05 weight %, based on the total weight of the mouthwash composition. Further optionally, the silicone oil is present in an amount of from 0.0001 to 0.005 weight %, based on the total weight of the mouthwash composition. Further optionally, the silicone oil is present in an amount of from 0.00015 to 0.0005 weight %, based on the total weight of the mouthwash composition. Still further optionally, the silicone oil is present in an amount of from 0.00015 to 0.00035 weight %, based on the total weight of the mouthwash composition.

Optionally, the silicone oil is present in an amount of from 0.0003 to 0.1 weight %, based on the total weight of the mouthwash composition.

Optionally, the silicone oil is a linear polysiloxane fluid. Further optionally, the linear polysiloxane fluid is substituted with alkyl groups, aryl groups, hydroxyl groups, or combinations thereof. Still further optionally, the linear polysiloxane fluid is substituted with alkyl groups. Yet further optionally, the silicone oil is selected from polydimethylsiloxane, hydroxy terminated polydimethylsiloxane, hexamethyldisiloxane, and polysiloxane polyether copolymers. Further optionally, the silicone oil is polydimethylsiloxane.

Optionally, the silicone oil is a cyclic polysiloxane fluid. Further optionally, the cyclic polysiloxane fluid is substituted with alkyl groups, aryl groups, hydroxyl groups, or combinations thereof. Still further optionally, the cyclic polysiloxane fluid is substituted with alkyl groups. Yet further optionally, the cyclic polysiloxane fluid is cyclomethicone.

Optionally, the packaged mouthwash composition further comprises one or more surfactants.

Optionally, the one or more surfactants are present in a total concentration of from 0.001 to 0.1 weight %, based on the total weight of the composition.

Optionally, the one or more surfactants is a non-ionic surfactant.

Optionally, the oil phase comprises one or more of: colorants, flavorants, and oil-soluble active ingredients.

Optionally, the aqueous phase comprises one or more of: humectants, phosphate salts, sweetening agents, preservatives, colorants, whitening agents, antisensitivity agents, zinc salts, tin salts, antibacterial agents, fluoride ion sources, water-soluble or water-dispersible polymers, ethanol, and tartar control agents.

Optionally, the composition comprises less than 5 weight % emulsion, based on the total weight of the composition. Further optionally, the composition comprises less than 3 weight % emulsion, based on the total weight of the composition.

In a second aspect, the present invention also provides the use, in a mouthwash composition, of a silicone oil to increase the cosmetic acceptability of the composition, wherein the mouthwash is contained within a container and comprises an aqueous phase and an oil phase, the aqueous phase being present as a first bulk layer and the oil phase being present as a second bulk layer, the first and second bulk layers being in contact with one another at an interface, with one of said layers being disposed on top of the other of said layers in the container.

The present invention also provides the use, in a mouthwash composition, of a silicone oil to reduce foaming of the composition, wherein the mouthwash is contained within a container and comprises an aqueous phase and an oil phase, the aqueous phase being present as a first bulk layer and the oil phase being present as a second bulk layer, the first and second bulk layers being in contact with one another at an interface, with one of said layers being disposed on top of the other of said layers in the container.

Optionally, the second bulk layer is disposed on top of the first bulk layer in the container.

Optionally, the silicone oil is present in the aqueous phase.

Optionally, the silicone oil is present in the oil phase.

Optionally, the silicone oil is present in the mouthwash composition in an amount of from 0.00005 to 0.1 weight %, based on the total weight of the composition. Further optionally, the silicone oil is present in the mouthwash composition in an amount of from 0.00005 to 0.05 weight %, based on the total weight of the composition. Further optionally, the silicone oil is present in the mouthwash composition in an amount of from 0.0001 to 0.005 weight %, based on the total weight of the composition. Further optionally, the silicone oil is present in the mouthwash composition in an amount of from 0.00015 to 0.0005 weight %, based on the total weight of the composition. Still further optionally, the silicone oil is present in the mouthwash composition in an amount of from 0.00015 to 0.00035 weight %, based on the total weight of the composition.

Optionally, the silicone oil is present in the mouthwash composition in an amount of from 0.0003 to 0.1 weight %, based on the total weight of the mouthwash composition.

Optionally, the silicone oil is a linear polysiloxane fluid. Further optionally, the linear polysiloxane fluid is substituted with alkyl groups, aryl groups, hydroxyl groups, or combinations thereof. Still further optionally, the linear polysiloxane fluid is substituted with alkyl groups. Yet further optionally, the silicone oil is selected from polydimethylsiloxane, hydroxy terminated polydimethylsiloxane, hexamethyldisiloxane, and polysiloxane polyether copolymers. Further optionally, the silicone oil is polydimethylsiloxane.

Optionally, the silicone oil is a cyclic polysiloxane fluid. Further optionally, the cyclic polysiloxane fluid is substituted with alkyl groups, aryl groups, hydroxyl groups, or combinations thereof. Still further optionally, the cyclic polysiloxane fluid is substituted with alkyl groups. Yet further optionally, the cyclic polysiloxane fluid is cyclomethicone.

Optionally, the composition comprises less than 5 weight % emulsion, based on the total weight of the composition. Further optionally, the composition comprises less than 3 weight % emulsion, based on the total weight of the composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Unless otherwise specified, all experiments and methods were carried out at 25° C. and at atmospheric pressure.

As discussed above, packaged dual phase mouthwash compositions having two visibly distinct layers (one on top of the other) have a tendency to develop a cloudy appearance over time, once the consumer has commenced use of a particular container of the mouthwash. When using these compositions, the consumer agitates the container (e.g. by shaking) in order to mix the two layers thoroughly, and then dispenses the required amount of the mouthwash. Upon subsequently leaving the container to stand with no further agitation, the composition once again settles out into the two visibly distinct layers. However, although the two layers may initially be transparent in appearance, these compositions have a tendency to develop a cloudy appearance upon settling out of the two layers after their mixing as described above. Also, problems of increased opacity of the composition can arise upon manufacture, as a result of high-speed filling of the two layers into the mouthwash container, and also during shipping of the product to retail outlets.

The present inventors have surprisingly found that the addition of silicone oil to a dual phase mouthwash composition improves cosmetic stability of the mouthwash composition. The cosmetic acceptability of the compositions is therefore improved. In particular, the present inventors have surprisingly found that the inclusion of silicone oil in the composition results in the transparent appearance of the oil phase being maintained even once the consumer has commenced use of the particular container of mouthwash. When the layers are allowed to settle out following their mixing (as described above), there is only minimal cloudiness observed in the oil phase layer (i.e. no consumer-unacceptable levels of cloudiness observed). Without being bound by any theory, it is believed that suppression of foam by the silicone oil when the mouthwash container is agitated or shaken by the consumer during use may contribute towards the improved cosmetic stability and increased cosmetic acceptability of the compositions (the improved cosmetic stability, and increased cosmetic acceptability, being indicated by there being no cloudiness or only minimal cloudiness observed in the aqueous or oil phases—particularly the oil phase—following settling of the compositions in their containers following agitation). Suppression of foam after high speed filling of containers with the mouthwash during manufacture, and during shipping from the manufacturing site to retail, may also contribute to the improvement in cosmetic stability.

Accordingly, the present invention provides a packaged mouthwash composition, the mouthwash composition comprising an aqueous phase and an oil phase;

wherein the mouthwash composition is contained within a container, the aqueous phase being present as a first bulk layer and the oil phase being present as a second bulk layer, the first and second bulk layers being in contact with one another at an interface, with one of said layers being disposed on top of the other of said layers in the container;

and wherein the mouthwash composition comprises a silicone oil.

In some embodiments, the aqueous phase and the oil phase are present as separate bulk layers, with the aqueous phase being present as the first bulk layer and the oil phase being present as the second bulk layer, when: (i) the composition is in a resting state prior to being subjected to agitation (agitation being, for example, shaking of the container); and/or (ii) the composition has been allowed to stand for 30 minutes following agitation (agitation being, for example, shaking of the container).

In certain embodiments, the second bulk layer is disposed on top of the first bulk layer in the container. In other embodiments, the first bulk layer is disposed on top of the second bulk layer in the container.

In some embodiments, the silicone oil is in the aqueous phase. In some embodiments, the silicone oil is in the oil phase. In some embodiments, the composition comprises more than one silicone oil.

In some embodiments the mouthwash composition comprises an amount of water from 60 to 95 weight %; from 65-85 weight %; from 70 to 80 weight %; from 75 to 80 weight %, and all ranges and sub ranges there between. In some embodiments the mouthwash composition comprises an amount of oil phase from 5 to 30 weight %, from 10 to 20 weight %, from 10 to 15 weight %; and all ranges and sub ranges there between.

Silicone oils as referred to herein are liquid polymerized siloxanes (which contain repeating Si—O—Si linkages) with organic groups attached to the Si atoms. Polysiloxane fluids (liquid polymerized siloxanes) useful herein include those with a viscosity, at 25° C., of about 1 milliPascal-sec (mPa-s) to about 1000 mPa-s, or about 2 mPa-s to about 500 mPa-s, or about 20 mPa-s to about 400 mPa-s as tested using a Brookfield viscometer. Polysiloxane fluids which may be used in the present invention can be linear or cyclic, and may be substituted with a wide variety of substituents. In some embodiments, the polysiloxane fluid is substituted with alkyl groups, aryl groups, hydroxyl groups, or combinations thereof. In certain embodiments, substituents include methyl, ethyl and phenyl substituents. Suitable polysiloxane fluids include linear polysiloxane polymers such as dimethicone (polydimethylsiloxane (PDMS), which has the formula $CH_3[Si(CH_3)_2O]_nSi(CH_3)_3$), hexamethyldisiloxane (which has the formula $(CH_3)_3SiOSi(CH_3)_3$) and other low viscosity analogues of the polysiloxane materials, in certain embodiments having a viscosity, at 25° C., of 200 mPa-s or less as tested using a Brookfield viscometer; and cyclic polysiloxanes such as cyclomethicone, and other cyclic siloxanes having for example a viscosity, at 25° C., of 200 mPa-s or less as tested using a Brookfield viscometer. Other fluids include polysiloxane polyether copolymers and hydroxy terminated polydimethylsiloxane fluid (e.g., Dow Corning ST-DIMETHICONOL™ 40, Dow Corning SGM 36, SGM3). Commercial examples of materials that are suitable for use herein include DC200 series fluids marketed by Dow-Corning Corporation and the AK Fluid series marketed by Wacker-Chemie GmbH, München, Germany. High molecular silicone resins with a polysiloxane blend may also be used including powdered trimethylsiloxysilicate, for example, Dow Corning 593 fluid, Wacker Belsil TMS 803. Another suitable silicone fluid from Dow Corning is Q7-9210. Also suitable is Xiameter® APE-1520 (a silicone emulsion).

In some embodiments (particularly those where the silicone oil is in the aqueous phase), the silicone oil is a water-dispersible silicone oil. In some embodiments, the silicone oil is provided as a dispersion in water (for example, Xiameter® AFE-1520 Antifoam Emulsion, from Dow Corning Corporation, which comprises 15 to 35 weight % PDMS dispersed in water)

In some embodiments, the silicone oil is present in an amount of from 0.00001 to 0.1 weight %; from 0.00005 to 0.1 weight %; from 0.00005 to 0.05 weight %; from 0.0001 to 0.005 weight %; from 0.00015 to 0.0005 weight %; from 0.00015 to 0.00035 weight %; or about 0.0002 weight %, based on the total weight of the mouthwash composition. In some embodiments, the silicone oil is present in an amount of from 0.0003 to 0.1 weight %, based on the total weight of the mouthwash composition. Where the silicone oil is provided as a solution or dispersion, for example PDMS as a 20 weight % dispersion in water, the amount of silicone oil is calculated as the active weight of the silicone oil, e.g. for a composition comprising 1 weight % PDMS (as a 20 weight % aqueous dispersion), the concentration of PDMS in the composition is 0.2 weight %.

In some embodiments, the composition comprises less than 5 weight %, less than 4.5 weight %, less than 4 weight %, less than 3.5 weight %, less than 3 weight %, less than 2.5 weight %, less than 2 weight %, less than 1.5 weight %, less than 1 weight %, or less than 0.5 weight % emulsion, based on the total weight of the composition. The composition may thus comprise less than 5 weight % of an emulsion formed between the aqueous phase and the oil phase, or less than 4.5 weight %, less than 4 weight %, less than 3.5 weight %, less than 3 weight %, less than 2.5 weight %, less than 2 weight %, less than 1.5 weight %, less than 1 weight %, or less than 0.5 weight % of such an emulsion, based on the total weight of the composition.

In certain embodiments, the first bulk layer may comprise ingredients which are themselves emulsions (e.g. oil-in-water emulsions) and/or the second bulk layer may comprise ingredients which are themselves emulsions (e.g. water-in-oil emulsions); however, the first and second bulk layers are still present as separate bulk layers as discussed above.

In certain embodiments, the packaged mouthwash composition further comprises one or more surfactants. Any orally acceptable surfactant can be used. In some embodiments, the one or more surfactants may include anionic, nonionic and/or amphoteric surfactants. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isethionate, sodium laureth carboxylate and sodium dodecyl benzenesulfonate. Suitable amphoteric surfactants include without limitation, derivatives of $C_{8-20}$ aliphatic secondary and tertiary amines having an anionic group such as carboxylate, sulfate, sulfonate, phosphate or phosphonate. Betaines may also be used, a suitable example of which is cocoamidopropyl betaine. In certain embodiments, the composition comprises a nonionic surfactant. Suitable nonionic surfactants include without limitation poloxamers; polyoxyethylene sorbitan esters such as Polysorbate 20 (polyoxyethylene (20) sorbitan monolaurate) or Polysorbate 80 (polyoxyethylene (20) sorbitan monooleate); fatty alcohol ethoxylates; alkylphenol ethoxylates; tertiary amine oxides; tertiary phosphine oxides; dialkyl sulfoxides and the like. In certain embodiments, one or more surfactants are present in a total amount of 0.001 to 1 weight %; from 0.005 to 0.5 weight %; from 0.01 to 0.1 weight %; from 0.015 to 0.05 weight %; or about 0.02 weight %, by total weight of the composition. The surfactants may be present in the aqueous phase, in the oil phase, or in both the oil phase and the aqueous phase. In certain embodiments, the composition comprises a nonionic surfactant in the aqueous phase in an amount of from 0.01 to 0.1 weight %, from 0.015 to 0.05 weight %; or about 0.02 weight %, by total weight of the composition. In some embodiments, the non-ionic surfactant is a polyoxyethylene sorbitan ester. In some embodiments, the non-ionic surfactant is Polysorbate 20.

In certain embodiments, the aqueous phase comprises one or more of: humectants, phosphate salts (such as sodium phosphate monobasic and sodium phosphate dibasic), sweetening agents, preservatives (such as potassium sorbate, benzoic acid, sodium benzoate, methylisothiazotinone), colorants, whitening agents (such as hydrogen peroxide, urea peroxide, sodium percarbonate), antisensitivity agents, zinc salts (such as zinc chloride, zinc lactate, zinc acetate, zinc citrate), tin salts, antibacterial agents (such as cetyl pyridinium chloride, triclosan, chlorhexidine), fluoride ion sources, water-soluble or water-dispersible polymers, ethanol, and tartar control agents.

In some embodiments, the oil phase comprises one or more of: colorants, flavorants, or certain oil-soluble actives (such as, for example, triclosan or bisabolol). In certain embodiments, the oil phase comprises mineral oil as a carrier.

Example of humectants which may be included in the compositions of the present invention include, but are not limited to, glycerin, sorbitol (optionally as a 70 weight % solution in water), xylitol, propylene glycol or low molecular weight polyethylene glycols (PEGs). Some humectants also function as sweeteners. One or more humectants are optionally present in a total amount of from 0.05 to 20 weight %, from 0.05 to 10 weight %, from 0.1 to 5 weight %, or from 1 to 3 weight %, based on the total weight of the composition.

Examples of sweetening agents which may be used in the compositions of the present invention include, for example, saccharin and salts thereof (such as sodium saccharin) and sucralose. One or more sweeteners are optionally present in a total amount depending strongly on the particular sweetener(s) selected, but typically 0.005 to 5 weight %, by total weight of the composition, optionally 0.005 to 0.2 weight %, further optionally 0.05 to 0.1 weight % by total weight of the composition.

Examples of antisensitivity agents include, but are not limited to, potassium salts such as potassium nitrate, potassium bicarbonate, potassium chloride, potassium citrate, and potassium oxalate; capsaicin; eugenol; strontium salts; chloride salts and combinations thereof. Such agents may be added in effective amounts, e.g., from about 1 weight % to about 20 weight % by weight based on the total weight of the composition, depending on the agent chosen. Antisensitivity agents may be included in the aqueous phase and/or the oil phase.

Examples of suitable fluoride ion sources include, but are not limited to: stannous fluoride, sodium fluoride, potassium fluoride, potassium monofluorophosphate, sodium monofluorophosphate (NaMFP), ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 weight % to about 10 weight %, e.g., from about 0.003 weight % to about 5 weight %, 0.01 weight % to about 1 weight %, or about 0.05 weight %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

Examples of tartar control (anticalculus) agents include, but are not limited to, phosphates and polyphosphates, polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

Examples of flavorants which may be used in the compositions of the present invention include, without limitation, tea flavours, vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaithol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 weight % to about 5 weight %, for example, from about 0.03 weight % to about 2.5 weight %, optionally about 0.05 weight % to about 1.5 weight %, further optionally about 0.1 weight % to about 0.3 weight % by total weight of the composition.

As indicated above, both the aqueous phase and the oil phase may comprise colorants. Colorants herein include pigments, dyes, lakes and agents imparting a particular luster or reflectivity. Any orally acceptable colorant can be used, including without limitation titanium dioxide, zinc oxide, red, yellow, brown and black iron oxides, ferric ammonium ferrocyanide, manganese violet, ultramarine, tianiated mica, bismuth oxychloride. Any suitable water-soluble colorant may be included in the aqueous phase, including (but not limited to) Blue #5, Blue #1, Yellow #6, Yellow #5 or Green #3. Any suitable oil-soluble colorant may be included in the oil phase, including (but not limited to) Violet #2. One or more colorants are optionally present in a total amount of from about 0.0001 weight % to about 10 weight %, for example, from about 0.001 weight % to about 5 weight %, or from about 0.01 weight % to about 2 weight %, based on the total weight of the composition.

In some embodiments, the aqueous phase comprises at least one bicarbonate salt useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. The one or more additional bicarbonate salts are optionally present in a total amount of 0.1 to 50 weight %, for example 1 to 20 weight %, by total weight of the composition.

The compositions of the present invention may comprise a saliva stimulating agent useful, for example, in amelioration of dry mouth. Saliva stimulating agents may be present in the aqueous phase, the oil phase, or in both the aqueous phase and the oil phase. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the invention may further comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof. These could be in the oil phase or in the aqueous phase, depending upon their solubility in each phase.

The present invention also provides the use, in a mouthwash composition, of a silicone oil to increase the cosmetic acceptability of the composition, wherein the mouthwash is contained within a container and comprises an aqueous phase and an oil phase, the aqueous phase being present as a first bulk layer and the oil phase being present as a second bulk layer, the first and second bulk layers being in contact with one another at an interface, with one of said layers being disposed on top of the other of said layers in the container.

The present invention also provides the use, in a mouthwash composition, of a silicone oil to reduce foaming of the composition, wherein the mouthwash is contained within a container and comprises an aqueous phase and an oil phase, the aqueous phase being present as a first bulk layer and the oil phase being present as a second bulk layer, the first and second bulk layers being in contact with one another at an interface, with one of said layers being disposed on top of the other of said layers in the container.

In some embodiments, the aqueous phase and the oil phase are present as separate bulk layers, with the aqueous phase being present as the first bulk layer and the oil phase being present as the second bulk layer, when: (i) the composition is in a resting state prior to being subjected to agitation (agitation being, for example, shaking of the container); and/or (ii) the composition has been allowed to stand for 30 minutes following agitation (agitation being, for example, shaking of the container).

In certain embodiments, the second bulk layer is disposed on top of the first bulk layer in the container. In other embodiments, the first bulk layer is disposed on top of the second bulk layer in the container.

In some embodiments, the silicone oil is present in the aqueous phase. In some embodiments, the silicone oil is present in the oil phase. In some embodiments, the silicone oil is present in an amount of 0.00001 to 0.1 weight %; from 0.00005 to 0.1 weight %; from 0.00005 to 0.05 weight %; from 0.0001 to 0.005 weight %; from 0.00015 to 0.0005 weight %; from 0.00015 to 0.00035 weight %; or about 0.0002 weight %, based on the total weight of the mouthwash composition. In some embodiments, the silicone oil is present in an amount of 0.0003 to 0.1 weight %, based on the total weight of the mouthwash composition. As discussed above, where the silicone oil is provided as a solution or dispersion, for example PDMS as a 20 weight % dispersion in water, the amount of silicone oil is calculated as the active weight of the silicone oil, e.g. for a composition comprising 1 weight % PDMS (as a 20 weight % aqueous dispersion), the concentration of PDMS in the composition is 0.2 weight %. The silicone oils may be any of the silicone oils as discussed above regarding the compositions of the present invention.

In some embodiments, the composition comprises less than 5 weight %, less than 4.5 weight %, less than 4 weight %, less than 3.5 weight %, less than 3 weight %, less than 2.5 weight %, less than 2 weight %, less than 1.5 weight %, less than 1 weight %, or less than 0.5 weight % emulsion, based on the total weight of the composition. The composition may thus comprise less than 5 weight % of an emulsion formed between the aqueous phase and the oil phase, or less than 4.5 weight %, less than 4 weight %, less than 3.5 weight %, less than 3 weight %, less than 2.5 weight %, less than 2 weight %, less than 1.5 weight %, less than 1 weight %, or less than 0.5 weight % of such an emulsion, based on the total weight of the composition.

In certain embodiments, the first bulk layer may comprise ingredients which are themselves emulsions (e.g. oil-in-water emulsions) and/or the second bulk layer may comprise ingredients which are themselves emulsions (e.g. water-in-oil emulsions); however, the first and second bulk layers are still present as separate bulk layers as discussed above.

In either of the above uses, the mouthwash composition may be in accordance with any of the embodiments as discussed above regarding the compositions of the present invention.

An increase in the cosmetic acceptability of the composition may comprise reduced cloudiness in the composition upon settling after shaking of the container, and in particular may comprise reduced cloudiness in the oil phase of the composition upon settling after shaking of the container, as compared to a composition which does not contain the silicone oil. In some embodiments, a cosmetically acceptable composition may have no appearance of cloudiness in the aqueous phase and/or the oil phase upon settling after shaking of the container; and in particular may have no appearance of cloudiness in the oil phase upon settling after shaking of the container. In some embodiments, a cosmetically acceptable composition may have no appearance of cloudiness in the aqueous phase and/or the oil phase at the interface between the oil phase and the aqueous phase upon settling after shaking of the container; and in particular may have no appearance of cloudiness in the oil phase at the interface between the oil phase and the aqueous phase upon settling after shaking of the container. In some embodiments, a cosmetically acceptable composition may have a transparent appearance in the aqueous phase and/or the oil phase upon settling after shaking of the container; and in particular may have a transparent appearance in the oil phase upon settling after shaking of the container. In some embodiments, a cosmetically acceptable composition may have a transparent appearance in the aqueous phase and/or the oil phase at the interface between the oil phase and the aqueous phase upon settling after shaking of the container; and in particular may have a transparent appearance in the oil phase at the interface between the oil phase and the aqueous phase upon settling after shaking of the container.

EXAMPLES

Example 1

An internal panel of R&D researchers trained in the science of cosmetic evaluation was randomly selected. These panelists were asked to evaluate the cosmetic acceptability of the aqueous and the oil phases of three dual phase mouthwash formulations by a simple yes/no format with yes being a cosmetically acceptable mouthwash and no being a cosmetically unacceptable mouthwash. The results are shown in Tables 1 and 2, below.

In Tables 1 and 2, Formulation B is a dual phase mouthwash, which has an aqueous phase (first bulk layer) and an oil phase (second bulk layer, disposed on top of the first bulk layer in the container), and contains 0.02 weight % Polysorbate 20 surfactant in the aqueous phase. Formulation B does not contain silicone oil. Formulation A corresponds to Formulation B, but with the addition to the aqueous phase of 0.001 weight % polydimethylsiloxane dispersion (Xiameter® AFE-1520 which, according to the supplier's Material Safety Data Sheet, comprises 15.0-35.0 weight % polydimethylsiloxane, 70.0-90.0 weight % water, 1.0-5.0 weight % polyethylene glycol sorbitan tristearate, ≤1.8 weight % methylated silica, ≤1.6 weight % methylcellulose, and ≤1.6 weight % amorphous fumed silica). Formulation A therefore comprises 0.00015 to 0.00035 weight % polydimethylsiloxane, based on the total weight of the composition. Formulation C is a commercial two-phase formula (a two-phase mouthwash with a purple oil phase), which does not contain any silicone oil.

Table 1 shows the results obtained for the evaluation of the cosmetic acceptability of Formulations A, B and C in their containers prior to dispensing, and without any agitation (shaking) of the containers. For each phase, "y" indicates that the particular phase of the mouthwash was considered cosmetically acceptable (with no unacceptable levels of cloudiness), and "n" indicates that the particular phase of the mouthwash was considered cosmetically unacceptable (i.e. unacceptable levels of cloudiness). The oil phase is considered cosmetically acceptable if it is transparent with no (or minimal) cloudiness observed, particularly at the oil phase/aqueous phase interface; and is considered cosmetically unacceptable if it has a cloudy appearance, particularly at the oil phase/aqueous phase interface (i.e. the first bulk layer/second bulk layer interface).

The final row of Table 1 shows the percentage of "y" scores attained by each phase of Formulations A, B and C (referred to herein as the "acceptance rate").

TABLE 1

| Appearance of aqueous phase prior to dispensing | | | Appearance of oil phase prior to dispensing | | |
| --- | --- | --- | --- | --- | --- |
| A | B | C | A | B | C |
| y | y | n | y | y | y |
| y | y | y | y | y | y |
| y | y | y | y | y | y |
| y | y | y | y | y | y |
| y | y | y | y | y | y |
| 100% | 100% | 80% | 100% | 100% | 100% |

Table 2 shows the results obtained for the evaluation of the cosmetic acceptability of Formulations A, B and C after dispensing. The procedure was as follows: the container was shaken to mix the two phases, and a portion of mouthwash dispensed. The mouthwash remaining in the container was then allowed to stand for 24 hours, after which time the evaluation of the appearance of the oil and aqueous phases was carried out. Again, "y" indicates that the particular phase of the mouthwash was considered cosmetically acceptable, and "n" indicates that the particular phase of the mouthwash was considered cosmetically unacceptable. The criteria for the oil or aqueous phases being scored as "y" or "n" were as described above. The final row of Table 2 shows the percentage of "y" scores attained by each phase of Formulations A, B and C (referred to herein as the "acceptance rate")

TABLE 2

| Appearance of aqueous phase 24 hrs after dispensing | | | Appearance of oil phase 24 hrs after dispensing | | |
| --- | --- | --- | --- | --- | --- |
| A | B | C | A | B | C |
| y | y | n | y | y | n |
| y | y | n | y | n | n |

TABLE 2-continued

| Appearance of aqueous phase 24 hrs after dispensing | | | Appearance of oil phase 24 hrs after dispensing | | |
| --- | --- | --- | --- | --- | --- |
| A | B | C | A | B | C |
| y | y | y | y | n | n |
| y | y | y | y | y | n |
| y | y | n | y | y | n |
| 100% | 100% | 40% | 100% | 60% | 0% |

The data in Table 2 clearly indicates that the presence of silicone oil in the aqueous phase of a dual phase mouthwash increases the cosmetic acceptability of the mouthwash. The addition of silicone oil to the aqueous phase (which constitutes one of the visibly distinct bulk layers) results in the transparent appearance of the oil phase (which constitutes another visibly distinct bulk layer) being maintained even once the consumer has commenced use of the particular container of mouthwash. When the layers are allowed to settle out following their mixing (as described above), there is only minimal cloudiness observed in the oil phase layer. Without wishing to be bound by any theory, it is believed that the silicone oil suppresses the foam generated by the surfactant, which is manifested by a cloudy appearance in the oil phase (at the oil phase/aqueous phase interface). For the competitive benchmark product (C), the oil phase is no longer transparent after 24 hours following dispensing. 0% of panelists indicated a cosmetically acceptable product in terms of the oil phase of Formulation C, and only 40% of panelists reported that the aqueous phase of this formulation was acceptable. However, for the formulation of the present invention (Formulation A), which contains 0.00015-0.00035 weight % silicone oil, a 100% acceptance rate was obtained tier the oil phase and a 100% acceptance rate for the aqueous phase. Formulation B (no silicone oil) gave parity performance to Formulation A in terms of cosmetic stability of the aqueous phase, but was inferior to Formulation A in terms of oil phase cosmetic stability. The above data demonstrates that the addition of a silicone oil to a dual phase mouthwash dramatically improves its cosmetic stability.

What is claimed is:

1. A packaged mouthwash composition, the mouthwash composition comprising an aqueous phase and an oil phase;
    wherein the mouthwash composition is contained within a container, the aqueous phase being present as a first bulk layer and the oil phase being present as a second bulk layer, the first and second bulk layers being in contact with one another at an interface, with one of said layers being disposed on top of the other of said layers in the container;
    wherein the mouthwash composition comprises a silicone oil in an amount of from 0.00005 to 0.1 weight %, based on the total weight of the mouthwash composition; wherein the composition further comprises a polyoxyethylene sorbitan ester surfactant; and wherein the aqueous phase and the oil phase are transparent 24 hours after dispersing.

2. The packaged mouthwash composition of claim 1, wherein the second bulk layer is disposed on top of the first bulk layer in the container.

3. The packaged mouthwash composition of claim 1, wherein the silicone oil is in the aqueous phase.

4. The packaged mouthwash composition of claim 1, wherein the silicone oil is in the oil phase.

5. The packaged mouthwash composition of claim 1, wherein the silicone oil is present in an amount of from 0.00005 to 0.05 weight %, based on the total weight of the mouthwash composition.

6. The packaged mouthwash composition of claim 5, wherein the silicone oil is present in an amount of from 0.0001 to 0.005 weight %, based on the total weight of the mouthwash composition.

7. The packaged mouthwash composition of claim 6, wherein the silicone oil is present in an amount of from 0.00015 to 0.0005 weight %, based on the total weight of the mouthwash composition.

8. The packaged mouthwash composition of claim 7, wherein the silicone oil is present in an amount of 0.00015 to 0.00035 weight %, based on the total weight of the mouthwash composition.

9. The packaged mouthwash composition of claim 1, wherein the silicone oil is present in an amount of from 0.0003 to 0.1 weight %, based on the total weight of the mouthwash composition.

10. The packaged mouthwash composition of claim 1, wherein the silicone oil is a linear polysiloxane fluid.

11. The packaged mouthwash composition of claim 10, wherein the linear polysiloxane fluid is substituted with alkyl groups, aryl groups, hydroxyl groups, or combinations thereof.

12. The packaged mouthwash composition of claim 11, wherein the linear polysiloxane fluid is substituted with alkyl groups.

13. The packaged mouthwash composition of claim 12, wherein the silicone oil is selected from polydimethylsiloxane, hydroxy terminated polydimethylsiloxane, hexamethyldisiloxane, and polysiloxane polyether copolymers.

14. The packaged mouthwash composition of claim 13, wherein the silicone oil is polydimethylsiloxane.

15. The packaged mouthwash composition of claim 1, wherein the silicone oil is a cyclic polysiloxane fluid.

16. The packaged mouthwash composition of claim 15, wherein the cyclic polysiloxane fluid is substituted with alkyl groups, aryl groups, hydroxyl groups, or combinations thereof.

17. The packaged mouthwash composition of claim 16, wherein the cyclic polysiloxane fluid is substituted with alkyl groups.

18. The packaged mouthwash composition of claim 17, wherein the cyclic polysiloxane fluid is cyclomethicone.

19. The packaged mouthwash composition of claim 1, wherein the polyoxyethylene sorbitan ester surfactant is present in a total concentration of from 0.001 to 0.1 weight %, based on the total weight of the composition.

20. The packaged mouthwash composition of claim 19, wherein the polyoxyethylene sorbitan ester surfactant is present in a total concentration of from 0.015 to 0.05 weight %, based on the total weight of the composition.

21. The packaged mouthwash composition of claim 1, wherein the polyoxyethylene sorbitan ester surfactant is selected from polyoxyethylene (20) sorbitan monolaurate and polyoxyethylene (20) sorbitan monooleate, or mixtures thereof.

22. The packaged mouthwash composition of claim 1, wherein the polyoxyethylene sorbitan ester surfactant is in the aqueous phase.

23. The packaged mouthwash composition of claim 1, wherein the oil phase comprises one or more of: colorants, flavorants and oil-soluble active ingredients.

24. The packaged mouthwash composition of claim 1, wherein the composition comprises less than 5 weight % emulsion, based on the total weight of the composition.

25. The packaged mouthwash composition of claim 24, wherein the composition comprises less than 3 weight % emulsion, based on the total weight of the composition.

26. The packaged mouthwash composition of claim 1, wherein the aqueous phase comprises one or more of: humectants, phosphate salts, sweetening agents, preservatives, colorants, whitening agents, antisensitivity agents, zinc salts, tin salts, antibacterial agents, fluoride ion sources, water-soluble or water-dispersible polymers, ethanol, and tartar control agents.

27. The packaged mouthwash composition of claim 1, wherein the composition comprises more than one silicone oil.

* * * * *